（12） United States Patent
Kosterev et al.

(10) Patent No.: US 8,009,293 B2
(45) Date of Patent: Aug. 30, 2011

(54) MODULATION CANCELLATION METHOD IN LASER SPECTROSCOPY

(75) Inventors: Anatoliy A. Kosterev, Pearland, TX (US); Robert F. Curl, Houston, TX (US)

(73) Assignee: William Marsh Rice University, Houston, TX (US)

( * ) Notice: Subject to any disclaimer, the term of this patent is extended or adjusted under 35 U.S.C. 154(b) by 436 days.

(21) Appl. No.: 12/089,692

(22) PCT Filed: Nov. 9, 2006

(86) PCT No.: PCT/US2006/060738
§ 371 (c)(1),
(2), (4) Date: Aug. 12, 2008

(87) PCT Pub. No.: WO2007/056772
PCT Pub. Date: May 18, 2007

(65) Prior Publication Data
US 2009/0303476 A1 Dec. 10, 2009

(51) Int. Cl.
*G01N 21/00* (2006.01)
(52) U.S. Cl. .............. 356/432; 356/323; 356/128
(58) Field of Classification Search .............. 356/323, 356/432, 437, 481, 128, 130
See application file for complete search history.

(56) References Cited

U.S. PATENT DOCUMENTS

| | | | |
|---|---|---|---|
| 4,410,273 A | 10/1983 | Mantz et al. | |
| 4,899,053 A * | 2/1990 | Lai et al. | 356/437 |
| 4,922,747 A | 5/1990 | Wall | |
| 4,937,448 A | 6/1990 | Mantz et al. | |
| 5,674,698 A | 10/1997 | Zarling et al. | |
| 6,239,877 B1 | 5/2001 | Beauducel | |
| 6,330,064 B1 * | 12/2001 | Rieder | 356/481 |
| 6,466,806 B1 | 10/2002 | Geva et al. | |
| 7,277,178 B2 | 10/2007 | Shpantzer et al. | |
| 7,606,274 B2 * | 10/2009 | Mirov et al. | 372/20 |

OTHER PUBLICATIONS

Foreign communication from a related counterpart application—International Search Report and Written Opinion, PCT/US06/60738, Apr. 17, 2008, 8 pages.

Gianfrani, L, et al., "Isotope analysis of water by means of near-infrared dual-wavelength diode laser spectroscopy," Optics Express, Jun. 30, 2003, pp. 1566-1576, vol. 11, No. 13, OSA.

* cited by examiner

*Primary Examiner* — Gregory J Toatley
*Assistant Examiner* — Iyabo S Alli
(74) *Attorney, Agent, or Firm* — Conley Rose, P.C.; Rodney B. Carroll

(57) ABSTRACT

Novel methods and laser spectroscopic systems for accurately measuring the concentration of compounds are disclosed herein. The disclosed methods utilize a modulation cancellation technique resulting in a significantly increase in the sensitivity and accuracy of laser spectroscopic measurements. In general, the methods and systems utilize modulation phase-shifting and amplitude attenuation to cancel the signals detected from at least two modulated light beams. Thus, any signal detected will be directly proportional to the concentration measurement.

32 Claims, 2 Drawing Sheets

MODULATION CANCELLATION METHOD IN LASER SPECTROSCOPY

TECHNICAL FIELD OF THE INVENTION

The present invention relates to techniques in laser spectroscopy. More particularly, this invention relates to wavelength modulation spectroscopy.

BACKGROUND OF THE INVENTION

Concentration ratio measurements via laser spectroscopic methods have been in use for many years. The most commonly studied elements have been carbon ($^{13}C/^{12}C$), distantly followed by hydrogen (D/H). The two main measurement methods are based on emission spectra and absorption spectra. Initially, quantitative determination of concentration ratios via the emission spectra of molecular transitions was inaccurate and not useful. At the same time, the absorption spectra lacked the resolution needed to characterize overlapping but isotopically different molecular transitions. This was mainly due to lack of power at monochromatic wavelengths. With the advent of lasers in the late 1960's, this limiting factor was eliminated, and high-resolution characterization of polyatomic species with isotopic substitution was possible. It was not until the completion of laser absorption studies in controlled laboratory settings that quantitative emission studies became useful.

Laser isotopic studies of carbon in methane and other short chain hydrocarbons continued for academic purposes until the late 1980's. In the 1990's, little scientific work was done in the field of carbon isotopic measurements in hydrocarbon gases. Since the 1990's, the academic focus has shifted to laser isotopic studies of inorganic polyatomic molecules. Commercialized applications of $^{13}C/^{12}C$ measurements have been used in medical research (measuring exhaled carbon dioxide), and in geological research for determining inorganic characterization of water and carbon in sandstone/mudstones, pyrite, sphalerite, galena and calcite. In the analysis of exhaled $CO_2$, light emitted by a $CO_2$ laser is used to measure isotope ratios. Inorganically bound isotopes of sulfur, oxygen, and hydrogen have also been studied with lasers for geological and environmental purposes.

Although much improved, current laser spectroscopic methods still possess some shortcomings. For example, in the context of a sample that contains two chemical species A and B having concentrations [A] and [B], respectively, concentrations are typically calculated from measurements of very small deviations of R=[A]/[B] ratio from the same ratio $R_{st}$ in the reference (standard) sample. The most common application where such measurements are required is isotopomer abundance quantification. In this case, the deviation from standard is commonly expressed as $$\delta[\text{\textperthousand}] = \frac{R - R_{st}}{R_{st}} \times 1000 \quad (1)$$

The existing spectroscopic approaches to measure $\delta$ require precise separate measurements of the absorption lines for A and B with the subsequent numerical calculation of $\delta$. This approach requires an extremely high accuracy of measurement because practically important $\delta$ ranges are between ~1% to 0.1%. For example, in traditional approaches the required or desired measurement accuracy for [B] may be $10^{-4}$. In practice, making such precise measurements is extremely difficult due to small variations in temperature, pressure, and other external factors.

The most common tool for this type of measurements is a mass-spectrometer (MS). MS provides the required accuracy, but there are a number of shortcomings associated with this technology. Mass spectrometers are expensive, bulky and in general can not be used in the field. A sample preparation is required that can potentially affect the isotopic composition. Confusion between molecules or molecular fragments with similar masses is possible.

Infrared molecular absorption spectroscopy is considered as a viable alternative to MS, but few groups have succeeded in achieving the required accuracy even in laboratory experiments Current optical instrumentation for determination of isotopic composition is based on separate precise measurements of the strength of absorption lines corresponding to two isotopes with the subsequent numerical comparison. Hence, a small difference between isotopic compositions of the analyzed sample and the reference sample is determined as a difference between two large numbers (concentration ratios). Some of the issues adding to the error of such an approach are: the temperature and pressure dependence of the absorption line intensity; non-linearity of laser tuning; baseline distortions caused by spurious interference fringes and far wings of the irrelevant strong absorption lines; and isotopic fractionation in the sampling procedure.

Another problem with present laser spectroscopic techniques has been the detection of species with broad irresolvable absorption features, which is a characteristic of many polyatomic molecules. In such cases, a semiconductor laser usually can not be wavelength modulated with a swing sufficient to cover the whole absorption feature. Thus, detection of such molecules would require amplitude modulation of the laser radiation. The scattered and subsequently absorbed light creates an incoherent background, making low-level concentration measurements difficult.

Accordingly, there is a need for a simple method of accurately measuring small deviations in concentration ratios using laser spectroscopy. It is further desired to provide a laser spectroscopic method to detect minute concentrations of complex molecules.

SUMMARY OF THE INVENTION

Novel methods and laser spectroscopic systems for accurately measuring concentrations of compounds are disclosed herein. The disclosed methods utilize a modulation cancellation technique resulting in the detection of a signal which is directly proportional to $\delta$ in Equation 1. Thus, the disclosed methods and systems significantly increase the sensitivity and accuracy of laser spectroscopic measurements.

These and other needs in the art are addressed in one embodiment by a method for measuring a concentration of a first and a second compound in a sample composition. The method comprises providing at least a first and a second modulated light beam having a first and a second wavelength, respectively. The second modulated light beam is phase shifted from the first modulated light beam. The method also comprises passing the first and the second modulated light beam through a reference composition. The reference composition comprises a reference concentration of the first and the second compound. In addition, the method comprises detecting a reference signal resulting from the absorption of the first and second modulated light beam by the reference composition. Moreover, the method comprises adjusting the amplitude of the second modulated light beam such that no reference signal is detected. Additionally, the method comprises passing the first modulated light beam and the second modulated light beam through a sample composition. The method further comprises detecting a sample signal so as to measure the concentration of the first and the second compound in the sample composition.

In another embodiment, a method for measuring the concentration of a compound having a background wavelength and an absorption wavelength comprises providing at least a first and a second modulated light beam, wherein the second modulated light beam is phase shifted from the first modulated light beam. The method also comprises tuning the first modulated light beam to the background wavelength of the compound and the second modulated light beam to the absorption wavelength of the compound. Moreover, the method comprises tuning the amplitude of the second modulated light beam such that no signal is detected when the first and the second modulated light beam are passed through a composition lacking the compound. In addition, the method comprises passing the first and the second modulated light beam through a sample composition. The method further comprises detecting a signal indicative of the concentration of the compound in the sample composition.

In a further embodiment, a laser spectroscopic system comprises a first and a second light source. The first and said second light source emit a first and second modulated light beam, respectively. The second beam is phase shifted from the first modulated light beam. Furthermore, the system comprises a sample cell including a sample detector. The sample cell contains a sample composition comprising a first and a second compound. The first and said second modulated light beam pass through the sample cell. The system additionally comprises a reference cell including a reference detector. The reference cell contains a reference concentration of the first and the second compound. The first and said second modulated light beam pass through said reference cell. Moreover, the system comprises an attenuator coupled to said reference detector and said second light source. The attenuator controls the second light source to match the amplitude of the second modulated light beam to the amplitude of the first modulated light beam such that no signal is detected from the reference detector.

The foregoing has broadly outlined the features and technical advantages of the present invention in order that the detailed description of the invention that follows may be better, understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the scope of the invention as set forth in the appended claims.

BRIEF DESCRIPTION OF THE DRAWINGS

For a more complete understanding of the invention, reference is made to the accompanying drawings, wherein.

DETAILED DESCRIPTION

Figure 1:
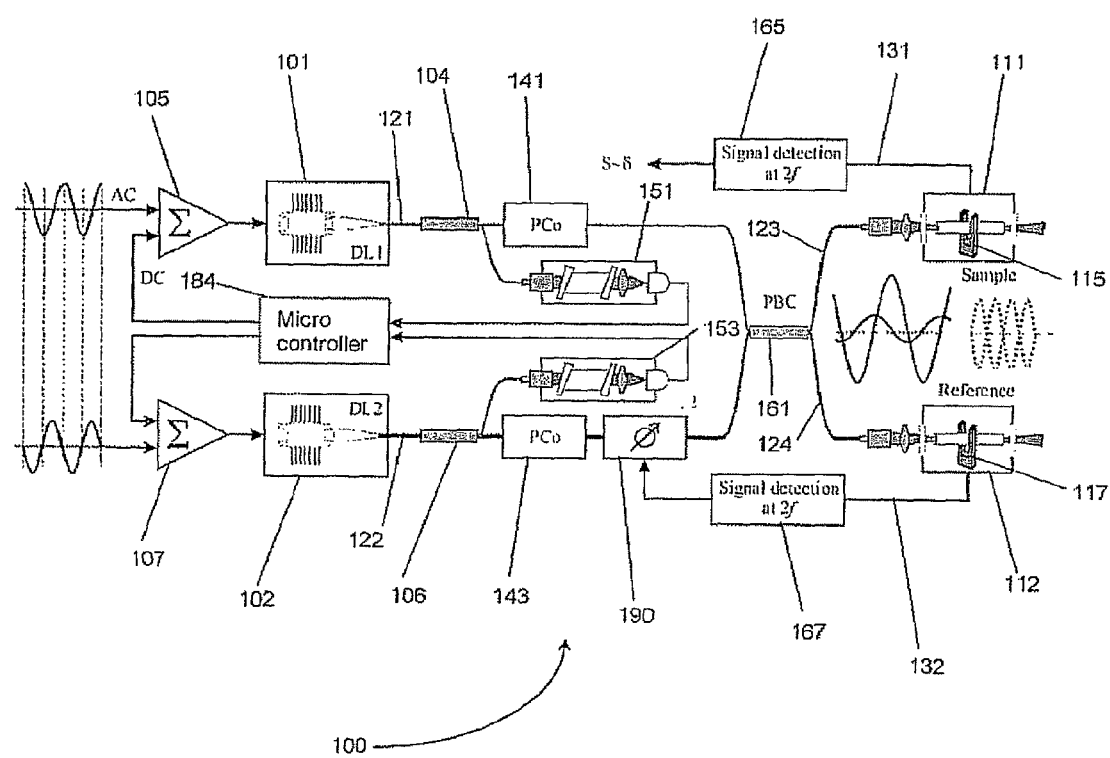
FIG. 1 is a schematic of a modulation cancellation method according to an embodiment of the invention.

Referring to FIG. 1, an embodiment of a laser spectroscopic system 100 is shown schematically and in general, includes first and second light sources 101, 102, a polarization combiner-splitter 161, a sample cell 111, and a reference cell 112. First and second light source 101, 102 typically each comprise a tunable laser device. However, first and second light source 101, 102 may comprise any suitable light emitting device. In certain embodiments, first and second light source 101, 102 comprise distributed-feedback diode lasers. Alternatively, first and second light source 101, 102 are quantum cascade lasers. First light source 101 generates a first modulated light beam 121 and second light source 102 generates a second modulated light beam 122. As defined herein, a modulated light bean is a beam of radiation in which the wavelength or amplitude of the beam of radiation is varied or modulated at a particular modulation frequency.

In further embodiments, laser spectroscopic system includes a first and second beam splitter 104, 106. First and second beam splitter 104, 106 split first and second beams 121, 122 and direct each respective beam to first and second polarization controllers 141, 143, and first and second calibration cells 151, 153, respectively. First and second cells 151, 153 typically each comprise a photodetector such as a photodiode, although other types of photodetectors may be utilized. In general, each cell 151, 153 contains a reference concentration of a compound. Specifically, first cell 151 contains a reference concentration of a first compound while second cell 153 contains a reference concentration of a second compound. The photodetector from each cell is coupled to a controller 184 which in turn is coupled to first and second current controllers 105, 107. First and second current controllers 105, 107 adjust the wavelength of first and second light sources 101, 102.

According to another embodiment, system 100 also includes a controller 184 such as a low-power digital signal microprocessor. However, any suitable microprocessors may be used with the laser spectroscopic system 100. Other examples of suitable processors include without limitation, field programmable gate arrays, microcontrollers, programmable logic devices, application specific integrated circuits and the like. As shown in FIG. 1, in an embodiment, controller 184 is coupled to reference cells 151, 153 and current controllers 104, 105 for line-locking first and second light source 101, 102. In other embodiments, additional controllers (not shown) may be coupled to first and second lock-in amplifiers and first and second light source 101, 102. The additional controllers may be used to calibrate or tune the modulation frequency of first and second modulated light beams 121, 122 in embodiments utilizing resonant acoustic detectors.

In embodiments, controller 184 includes memory. Memory may comprise volatile (e.g., random access memory) and/or non-volatile memory (e.g., read only memory (ROM), electrically-erasable programmable ROM (EEPROM), Flash memory, etch). In a preferred embodiment, memory is flash memory. Memory may be used to store data or code (e.g., software, discussed below) that is executed by the controller 184. The executable code may be executed directly from the non-volatile memory or copied to the volatile memory for execution therefrom Laser spectroscopic system 100 may also include memory external to controller 184. This external memory is generally coupled to controller 184 and may comprise either volatile or non-volatile memory.

In general, first and second compound may be any material or chemical. Additionally, the first and second compound may be a gas or a liquid. In preferred embodiments, the second compound is an isotope of the first compound. By way of example only, the first compound may comprise $H_2^{16}O$ while the second compound may comprise $H_2^{18}O$. Other examples of the first and second compounds include without limitation, $^{12}$C- and $^{13}$C-containing species, $^{32}$S- and $^{34}$S-containing species, $^{14}$N and $^{15}$N containing species, or H- and D-containing species.

In one embodiment, the system 100 includes a polarization combiner-splitter 161 which combines first and second beam 121, 122 into a combined beam (not shown) and splits it into a first and second combined beam 123, 124 as seen in FIG. 1. However, the first and second modulated light beams 121, 122 may be combined by any suitable means including, without limitation, a wavelength division multiplexer, a polarization combiner, or diffraction grating. In addition, the system 100 may incorporate a separate beam combiner and beam splitter to combine first and second beam 121, 122 and split the combined beam.

In at least one embodiment, the system 100 comprises an attenuator 190. Attenuator may be any device known to one of ordinary skill in the art used to adjust the intensity of a light beam. Depending on the embodiment, attenuator 190 may be used to adjust first or second beam 121, 122. In the embodiment shown in FIG. 1, attenuator is coupled to second lock-in amplifier 167. As will be described in more detail below, attenuator 190 may utilize signals from reference detector 117 via second lock-in amplifier 167 to adjust intensity of second beam 122.

In an embodiment, system 100 comprises a sample cell 111 and a reference cell 112. Sample and reference cells 111, 112 generally comprise sample and reference detectors 115, 117 which serve to detect signals from sample and reference cells 111, 112, respectively. In any case, first and second cells 111, 112 generate sample and reference output signals 131, 132, respectively. Moreover, sample and reference cell 111, 112 contain the sample and reference compositions, respectively. The sample composition generally comprises a concentration of the first and the second compound while the reference composition comprises a known or reference concentration ratio of the first and second compound. As will be described in further detail below, the described apparatus is used to determine whether the sample composition contains a concentration ratio of the compounds different than the reference composition.

According to one embodiment, sample and reference detectors 115, 117 are used to detect the absorption of the combined beams 123, 124 by the sample composition and the reference composition. More specifically, the detector 115 in sample cell 111 detects a signal generated because of the absorption of the first and second modulated light beam in combined beam by the sample composition. In a particular embodiment, detector 115 is an acoustic detector such as a microphone, a quartz tuning fork, etc. In other embodiments, detector 115 is a photodetector such as a photodiode. However, detector may be any suitable detector capable of detecting absorption of light by a compound. Similarly, reference detector 117 may comprise a photodetector, an acoustic detector, or any other suitable detector.

Sample detector 115 may be coupled to a first lock-in amplifier 165, Likewise, reference detector 117 may be coupled to a second lock-in amplifier 167. First lock-in amplifier 165 is generally coupled to an output device or a microprocessor to process the data generated from sample cell (not shown). On other hand, second lock-in amplifier 167 is typically coupled to an attenuator 190 as shown in FIG. 1. Attenuator 190 is preferably used to adjust the amplitude of second modulated light beam 122 in response to a signal received from second lock-in amplifier 167.

Figure 2:
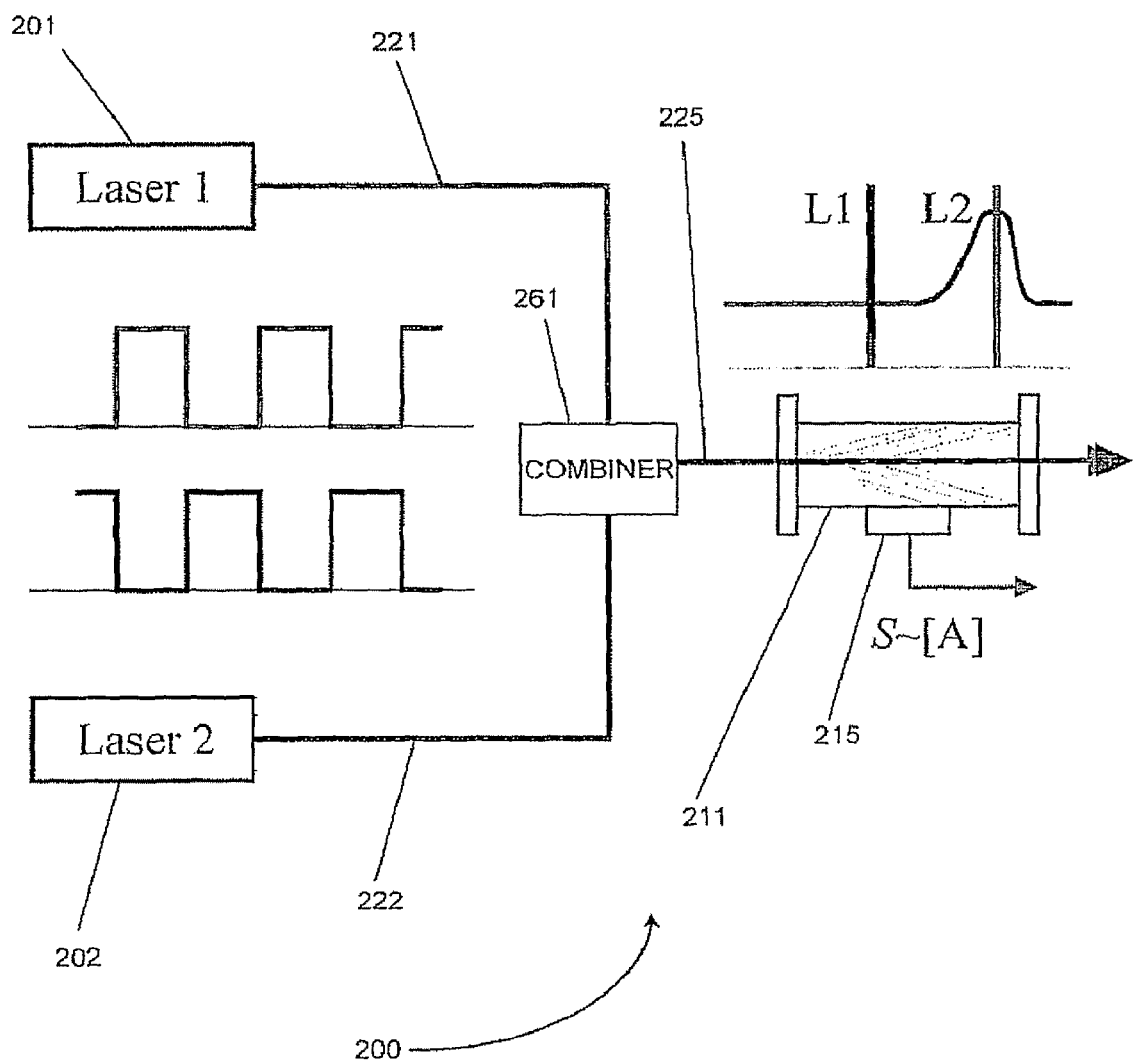
FIG. 2 is a schematic of a second embodiment of the present modulation cancellation method as applied to chemical species with broad unresolved species.

Another embodiment of a laser spectroscopic system 200 is shown in FIG. 2. Such an embodiment may be used to detect minute concentrations of complex, polyatomic molecules. In this embodiment, system 200 includes first and second light sources 201, 202, a beam combining device 261, and a sample cell 211. Beam combining device 261 may comprise a polarization combiner as described above. Sample cell 211 includes a detector 215. As with other embodiments, detector 215 may comprise an acoustic detector, a photodetector, or other suitable detector in this embodiment, system 200 does not require a dual line-locking feedback loop as shown in FIG. 1. Nor does system 200 implement a reference cell. Although not shown in FIG. 2, it is contemplated that other devices known to those of skill in the art for laser spectroscopy may be incorporated into system 200 such as microcontrollers, lock-in amplifiers, sensors, etc.

In one embodiment, a method of measuring a concentration of a first and a second compound in a sample composition comprises the following steps: a) providing at least a first and a second modulated light beam having a first and a second wavelength, respectively, wherein the second modulated light beam is phase shifted from the first modulated light beam; b) passing the first and the second modulated light beam through a reference composition, wherein said reference composition comprises a reference concentration of the first and the second compound; c) detecting a reference signal resulting from the absorption of the first and second modulated light beam by the reference composition; d) adjusting the amplitude of the second modulated light beam such that no reference signal is detected; e) passing the first modulated light beam and the second modulated light beam through a sample composition; and f) detecting a sample signal so as to measure the concentration of the first and a second compound in the sample composition.

Referring now to FIG. 1, in a preferred embodiment, first and second modulated light beams 121, 122 are wavelength-modulated or amplitude-modulated with the same modulation frequency f, but different phase. In other words, first and second modulated light beams 121, 122 generally have equal modulation frequencies, but opposite phase. However, other embodiments may incorporate different modulation frequencies. Unless otherwise noted, as defined herein, phase-shifting refers to adjusting or shifting the modulation phase of a light beam. As will be described in more detail below, the modulation of the second beam 122 may be phase-shifted 180° from first beam 121. However, second beam 122 may be phase-shifted to any appropriate phase to cancel a signal from first beam 121. For example, if the signals from sample and reference detector 115,117 are detected at twice the modulation frequency, the phase shift may be 90°. In some embodiments, injection current modulation may be imposed on top of the DC current that is used to power light sources 101, 102.

Hereinafter, the first and second compound to be measured are referred to as A and B while the concentration of first and second compound are denoted by [A] and [B]. In an embodiment, first and second modulated light beams 121, 122 are emitted from first and second light source 101, 102 and are directed to first and second beam splitters 104, 106. Preferably, the central wavelengths of first and second light source 101, 102 are tuned to the absorption wavelength of the first and second compound, A and B, respectively. Thus, the magnitude of the signal detected by a detector from first light source 101 after passing through the sample composition in sample cell 111 is dependent on the peak absorption and width of the spectroscopic line of A (in its turn, peak absorption is proportional to [A]), the radiation power from first light source 101, and the modulation depth of first light source 101. Similarly, the magnitude of the signal detected by a detector from second light source 101 after passing through a sample composition will depend on the peak absorption mid width of the spectroscopic line of 13 (in its turn, peak absorption is proportional to [B]), the radiation power from second light source 102, and the modulation depth of second light source 102.

The first and second beam 121, 122 are initially split to line-lock first and second light source 101, 102. More particularly, first calibration cell 151 contains a reference concentration of A while second calibration cell 153 contains a reference concentration of B. Photodetector in each calibration cell 151, 153 provides a signal at the wavelength at which A and B absorb light, respectively. For example, first calibration cell 151 may contain a reference concentration of $C^{12}$ and second calibration cell 153 may contain a reference concentration of $C^{13}$, a carbon isotope. The signals from the calibration cells 151, 153 are relayed to controller 184 to detect the wavelength error. Controller 184 performs a computation on the wavelength error signal, and sends this error factor to current controllers 105, 107 to adjust the wavelength of first and second light source 101, 102. This feedback loop ensures that first and second light sources 101, 102 are emitting light at the appropriate wavelength corresponding to the absorption lines of A and B in sample cell. This wavelength control is known as "line-locking." In particular embodiments, the line-locking may be accomplished by a 3f technique, where f is the wavelength modulation frequency of the light beam emitted from the light sources 101, 102.

In a further embodiment, after passing through beam splitters 104, 106, the polarization of the first and second beam 121, 122 may be altered or adjusted by passing the beams through polarization controllers 141, 143. The polarization controllers adjust polarization of first and second beam 121, 122 so that the beams may be combined by a polarization combiner or another appropriate device. In an embodiment, first and second beams 121, 122 are combined into a combined beam and then split into first and second combined beams 123, 124 by polarization combiner-splitter 161 as shown in FIG. 1. Each combined beam 123, 124 thus comprises both first and second beam 121, 122, preferably in identical proportions.

Preferably, first and second combined beam 123, 124 each have equal intensities. That is, combined beam is split evenly into first and second combined beam 123, 124. However, it is contemplated that other embodiments may utilize different ratios of intensity between first and second combined beam. First combined beam 123 is directed to sample cell 111 while second combined beam 124 is directed to reference cell 112. Because first and second beam 121, 122 are line-locked to first and second compound, respectively, as first and second combined beam pass through sample and reference cell 111, 122, the first and second compound present in both the sample and reference composition will absorb the energy from first and second beam in each combined beam. In an alternative embodiment, it is contemplated that the combined beam need not be split into first and second combined beam 113, 135, but instead a combined beam may pass through reference cell 112 and sample cell 111 in series (not shown).

The absorption of radiation by first and second compound is measured by sample and reference detectors 115, 117 in sample and reference cell 111, 112, respectively. As mentioned above, any suitable means may be utilized to measure the absorption signals detected in sample and reference cell 111, 112. According to one embodiment, the absorption of the combined beams 123, 124 by the sample composition and the reference composition may be detected by photoacoustic detection. More specifically, the detectors 115, 117 in sample cells 111, 112 detect an acoustic signal generated because of the absorption of the first and second modulated light beam in combined beam by the sample composition. In embodiments using photoacoustic detection, quartz tuning forks may be used in the reference and sample cells to measure the absorption signals. In other embodiments, photodetection may be used to detect absorption by the first and second compound.

After passing through second polarization controller 143, second modulated light beam 122 is directed at an attenuator 190 before entering polarization combiner 161. Alternatively, attenuator 190 may be placed before polarization controller 143 and thus, second modulated light beam 122 is directed to attenuator 190 before passing through polarization controller 143. In preferred embodiments, the intensity of second modulated light beam 122 may be adjusted by using attenuator 190 to null the signal from reference detector 117. In another embodiment, by adjusting the power $P_2$ of second beam 122 and/or its modulation depth, the corresponding signal may be made equal in magnitude but opposite in phase to the signal generated by absorption of first modulated light beam 121 to null the signal from reference detector 117.

As disclosed above, the modulation of second light source 102 is phase shifted with respect to the wave modulation of first light source 101. In some embodiments, such as 2f photoacoustic detection, second beam 122 is phase shifted by 90° such that the signals generated by first and second light source 101, 102 in the reference cell will be opposite in sign and cancel each other. Put another way, the two signals in the reference cell 112 are balanced in such a way that no generation of signal occurs and the detector 117, does not detect any signal $S_{ref}$:

$$S_{ref} = k_{ref}(P_1[A]_{ref} - P_2[B]_{ref}) = 0 \quad (2)$$

where $k_{ref}$ describes responsivity of the reference detector 117 and $P_1$, $P_2$ are optical powers of first and second light source 101, 102, respectively. The signal dependence on the modulation index has been omitted for simplicity, and the spectroscopic line peak absorbance is represented by the concentration of the corresponding species. It follows from (2) that $$P_2 = P_1[A]_{ref}/[B]_{ref} = P_1 R_{ref} \quad (3)$$

Without being limited by theory, it is believed that if the ratio $R=[A]/[B]$ is the same in sample cell 111 as $R_{ref}$ in reference cell 117 and both samples are at the similar pressure and temperature conditions, the balanced radiation will not generate the response in the sample detector 115 either. If R is not equal to $R_{ref}$, the sensor response gives:

$$S = k(P_1[A] - P_2[B]) \quad (4)$$

Simple substitutions using (3), (1), and the definition of R give:

$$S = 1/1000 \times k P_1[B] R_{ref} \times \delta \quad (5)$$

Thus, any signal measured from the sample detector 115 in FIG. 1 will be directly proportional to δ. In Equation (5) $R_{ref}$ is known by definition, $P_1$ is constant and can be either monitored directly or derived from $S_{ref}$ when second light source 102 is turned off, and k[B] can be derived from S when first light source 101 is off. In an alternative embodiment, the amplitude of first beam 121 may be adjusted using an attenuator (not shown) to adjust its amplitude or intensity with respect to the amplitude of second beam 122 to produce the same result above.

Any signal detected from sample detector is relayed to first lock-in amplifier 165 which is tuned to the modulation frequency of the light sources 101, 102. Likewise, signal from reference detector 117 is amplified by second lock-in amplifier 167 which is tuned to the modulation frequencies of the light sources 101, 102. Any signal detected from reference detector 117 indicates that the amplitude of second beam 122 needs to be attenuated. Accordingly, the signal from second lock-in amplifier is used in conjunction with attenuator 190 as part of a feedback loop to control the amplitude of second beam 122.

In another embodiment, a method for measuring the concentration of a compound having a background wavelength and an absorption wavelength comprises: a) providing at least a first and a second modulated light beam, wherein the second modulated light beam is phase shifted from the first modulated light beam, b) tuning the first modulated light beam to the background wavelength of the compound and the second modulated light beam to the absorption wavelength of the compound, c) tuning the amplitude of the second modulated light beam such that no signal is detected in the absence of the compound when the first and the second modulated light beam are passed through a sample composition, d) passing the first and the second modulated light beam through a sample composition, and e) detecting a signal indicative of the concentration of the compound in the sample composition.

Referring to FIG. 2, first modulated light beam 221 from first light source 201 may be tuned to the background wavelength of the compound's absorption spectrum, while the second modulated light beam 222 from second light source 202 may be tuned to a target compound's absorption wavelength. In a preferred embodiment, the modulation of second modulated light beam 222 is phase-shifted from the modulation of first modulated light beam 221. For example, second modulated light beam 222 may have a 180° phase shift from first modulated light beam 221. FIG. 2 shows an embodiment with rectangular amplitude modulation of light beams 221, 221, but the amplitude modulation may be sine or any other waveform. As above, the emissions of first light source 201 and second light source 202 may be combined to be collinear and form a combined beam 225 by using a polarization combiner or other suitable device. Combined beam 225 may pass through a sample cell 211 containing a sample composition with an unknown concentration of the target compound.

Furthermore, the modulation amplitudes of first and second modulated light beams 221, 222 may be adjusted or tuned such that no signal is detected in the absence of the target compound, A, in a sample composition. If the concentration [A] is not equal to zero, the signal detected at the modulation frequency will be proportional to the concentration [A].

A signal resulting from the absorption of the combined first and second light beams 221, 222 may be measured by any suitable means, including without limitation photoacoustic detection and photodiode detection. The target compound is preferably a compound that exhibits broad unresolved absorption features in laser spectroscopy. More particularly, the target compound may comprise a background wavelength and a target absorption wavelength. Such compounds are usually complex, polyatomic molecules. Without limitation, examples of such compounds include isoprene, nerve gases, hydrazine, rocket fuel components, or combinations thereof.

Although the present invention and its advantages have been described in detail, it should be understood that various changes, substitutions and alterations may be made herein without departing from the spirit and scope of the invention as defined by the appended claims.

What is claimed is:

1. A method of measuring a concentration of a first and a second compound in a sample composition comprising;
    a) providing at least first and second modulated light beams having first and second wavelengths, respectively, wherein the modulation of the second modulated light beam is phase shifted from the modulation of the first modulated light beam;
    b) passing the first and the second modulated light beams through a reference composition, wherein said reference composition comprises a reference concentration of the first and the second compound;
    c) detecting a reference signal resulting from the absorption of the first and second modulated light beams by the reference composition;
    d) adjusting the amplitude of the second modulated light beam such that no reference signal is detected;
    e) passing the first modulated light beam and the second modulated light beam through a sample composition; and
    f) detecting a sample signal so as to measure the concentration of the first and the second compound in the sample composition.

2. The method of claim 1, wherein (f) comprises detecting the sample signal using an acoustic detector.

3. The method of claim 1, wherein (f) comprises detecting the sample signal using a photodetector.

4. The method of claim 1, further comprising combining the first and second modulated light beams to form a combined beam before (b).

5. The method of claim 4, wherein combining the first and second modulated light beams comprises passing the first and second modulated light beams through a wavelength division multiplexer, a polarization combiner, or diffraction grating.

6. The method of claim 4, further comprising splitting the combined beam to form first and second combined beams.

7. The method of claim 6, wherein (b) comprises passing the second combined beam through the reference composition and (e) comprises passing the first combined beam through the sample composition.

8. The method of claim 1, wherein steps b) and e) are carried out in parallel.

9. The method of claim 1, wherein steps b) and e) are carried out in series.

10. The method of claim 1, wherein the first wavelength is equal to the absorption wavelength of the first compound and the second wavelength is equal to the absorption wavelength of the second compound.

11. The method of claim 1, further comprising line-locking the first and the second modulated light beams to the first and the second wavelengths, respectively.

12. The method of claim 1, wherein the first and the second modulated light beams are wavelength modulated or amplitude modulated.

13. The method of claim 1, wherein the first and the second modulated light beams have equal modulation frequencies.

14. The method of claim 1, wherein the reference composition and sample composition are gaseous.

15. The method of claim 1, wherein the reference composition and sample composition are liquid.

16. The method of claim 1, wherein the first and second modulated light beams are provided by at least one tunable laser source.

17. The method of claim 16, wherein the at least one tunable laser source comprises a distributed-feedback diode or quantum cascade laser.

18. The method of claim 1, wherein the modulation of the first and the second modulated light beams are phase-shifted 90°.

19. The method of claim 1, wherein the first and the compound comprise $^{12}$C- and $^{13}$C-containing species, $^{32}$S- and $^{34}$S-containing species, $^{14}$N and $^{15}$N containing species, or H- and D-containing species, respectively.

20. A method for measuring the concentration of a compound having a background wavelength and an absorption wavelength, said method comprising:
 a) providing at least first and second modulated light beams, wherein the modulation of second modulated light beam is phase shifted from the modulation of the first modulated light beam;
 b) tuning the first modulated light beam to the background wavelength of the compound and the second modulated light beam to the absorption wavelength of the compound;
 c) tuning the amplitude of the second modulated light beam such that no signal is detected when the first and the second modulated light beams are passed through a composition lacking the compound;
 d) passing the first and the second modulated light beams through a sample composition; and
 e) detecting a signal indicative of the concentration of the compound in the sample composition.

21. The method of claim 20, further comprising combining the first and second modulated light beams to form a combined beam before (d).

22. The method of claim 21, wherein (d) comprises passing the combined beam through the sample composition.

23. The method of claim 21, wherein combining the first and second modulated light beams comprises passing the first and second modulated light beams through a wavelength division multiplexer, a polarization combiner, or diffraction grating.

24. The method of claim 20, wherein (e) comprises detecting a signal by photoacoustic detection.

25. The method of claim 20, wherein (e) comprises detecting a signal by photodiode detection.

26. The method of claim 20, wherein the second wavelength comprises the background wavelength of the compound.

27. The method of claim 20, wherein the first wavelength comprises the absorption wavelength of the compound.

28. The method of claim 20, wherein the first modulated light beam is phase-shifted 180° from second modulated light beam.

29. The method of claim 20, wherein the compound comprises a nerve gas, a rocket fuel component, hydrazine, or isoprene.

30. A laser spectroscopic system comprising:
 a first and a second light source, wherein said first and said second light source emit first and second modulated light beams, respectively, wherein the modulation of said second modulated light beam is phase shifted from the modulation of said first modulated light beam;
 a sample cell comprising a sample detector, wherein said sample cell contains a sample composition comprising a first and a second compound, wherein said first and said second modulated light beams pass through said sample cell;
 a reference cell comprising a reference detector, wherein said reference cell contains a reference concentration of the first and the second compound, wherein said first and said second modulated light beams pass through said reference cell; and
 an attenuator coupled to said reference detector and said second light source, wherein said attenuator controls the second light source to match the amplitude of the second modulated light beam to the amplitude of the first modulated light beam such that no signal is detected from the reference detector.

31. The system of claim 30, wherein the sample detector and the reference detector comprise acoustic detectors.

32. The system of claim 30, wherein the sample detector and the reference detector comprise photodetectors.

\* \* \* \* \*